US 6,645,749 B2

(12) United States Patent
Vind

(10) Patent No.: US 6,645,749 B2
(45) Date of Patent: Nov. 11, 2003

(54) LIPOLYTIC ENZYME

(75) Inventor: Jesper Vind, Vaeflose (DK)

(73) Assignee: Novozymes A/S, Bagsvaerd (DK)

( * ) Notice: Subject to any disclaimer, the term of this patent is extended or adjusted under 35 U.S.C. 154(b) by 111 days.

(21) Appl. No.: 09/931,401

(22) Filed: Aug. 16, 2001

(65) Prior Publication Data

US 2003/0003561 A1 Jan. 2, 2003

(30) Foreign Application Priority Data

May 28, 2001 (DK) .......................................... 2001 00843

(51) Int. Cl.[7] .............................. C12N 9/20; C07H 21/04
(52) U.S. Cl. ........................ 435/198; 435/195; 435/196; 435/197; 435/252.33; 435/320.1; 536/23.2; 536/23.1; 536/23.74
(58) Field of Search ................................ 435/195, 197, 435/196, 198, 252.33, 320.1; 536/23.2, 23.1, 23.74

(56) References Cited

U.S. PATENT DOCUMENTS 5,990,069 A    11/1999   Andre et al. ................. 510/281

FOREIGN PATENT DOCUMENTS

| WO | WO 90/09446 | * | 8/1990 |
| WO | WO 98/26057 |   | 6/1998 |

* cited by examiner

*Primary Examiner*—Nashaat T. Nashed
(74) *Attorney, Agent, or Firm*—Elias Lambiris; Jason Garbell

(57) ABSTRACT

The present invention is directed to phospholipase from *Fusarium solani* (MUCL38667) and analogues thereof, nucleic acid constructs, recombinant expression vectors, and recombinant host comprising the nucleic acid sequences encoding the phospholipase from *Fusarium solani* (MUCL38667) and analogues thereof, methods of making same, and method of using the phosopholipases of the present invention in baking methods, baking compositions and detergent compositions.

9 Claims, No Drawings

SEQUENCE LISTING

```
<160> NUMBER OF SEQ ID NOS: 13

<210> SEQ ID NO 1
<211> LENGTH: 1150
<212> TYPE: DNA
<213> ORGANISM: Fusarium solani
<220> FEATURE:
<221> NAME/KEY: CDS
<222> LOCATION: (365)..(1147)
<223> OTHER INFORMATION:
<220> FEATURE:
<221> NAME/KEY: Intron
<222> LOCATION: (94)..(148)
<223> OTHER INFORMATION:
<220> FEATURE:
<221> NAME/KEY: Intron
<222> LOCATION: (317)..(364)
<223> OTHER INFORMATION:
<220> FEATURE:
<221> NAME/KEY: sig_peptide
<222> LOCATION: (1)..(93)
<223> OTHER INFORMATION:
<220> FEATURE:
<221> NAME/KEY: CDS
<222> LOCATION: (1)..(93)
<223> OTHER INFORMATION:
<220> FEATURE:
<221> NAME/KEY: mat_peptide
<222> LOCATION: (149)..()
<223> OTHER INFORMATION:
<220> FEATURE:
<221> NAME/KEY: CDS
<222> LOCATION: (149)..(316)
<223> OTHER INFORMATION:

<400> SEQUENCE: 1 atg cgc ctg ctt cct ctc ctc tcg gtc gta acg ctc act gcg gcg agt      48
Met Arg Leu Leu Pro Leu Leu Ser Val Val Thr Leu Thr Ala Ala Ser
    -30                 -25                 -20 cct ata gcc tcc gtc cag gag tac act gac gcc ttg gag aag aga          93
Pro Ile Ala Ser Val Gln Glu Tyr Thr Asp Ala Leu Glu Lys Arg
-15                 -10                  -5                  -1 ggtaaccacc aacactcccc taagacagac ctcgccctaa caagtaaact ctagt gct     151
                                                                Ala
                                                                  1 atc acc gcc tct caa ctt gac tat gaa aac ttc aag ttt tac atc cag      199
Ile Thr Ala Ser Gln Leu Asp Tyr Glu Asn Phe Lys Phe Tyr Ile Gln
            5                   10                  15 cac ggt gcc gca gcg tat tgc aac tct gag acg gcc tct ggt caa aaa      247
His Gly Ala Ala Ala Tyr Cys Asn Ser Glu Thr Ala Ser Gly Gln Lys
        20                  25                  30 ata acc tgc aac gac aac ggc tgc aaa ggc atc gag gcc aac aac gcc      295
Ile Thr Cys Asn Asp Asn Gly Cys Lys Gly Ile Glu Ala Asn Asn Ala
    35                  40                  45 ata atc gta gca tcc ttc gtg taagctcccc tttcccctca cggaaccctt         346
Ile Ile Val Ala Ser Phe Val
```

```
                                                                          50                          55
caactgacac gtagcagc ggc acg ggc act ggc atc gga ggc tac gtc tcc            397
                    Gly Thr Gly Thr Gly Ile Gly Gly Tyr Val Ser
                                        60                  65 act gac aat gtc cgt aag gag att gtc ctc tcg att cgc ggc agc agc            445
Thr Asp Asn Val Arg Lys Glu Ile Val Leu Ser Ile Arg Gly Ser Ser
            70                  75                  80 aac atc cgc aac tgg ctc acc aac gtc gac ttt ggc cag tcc agc tgc            493
Asn Ile Arg Asn Trp Leu Thr Asn Val Asp Phe Gly Gln Ser Ser Cys
85                  90                  95 tcc tac gtc cgc gac tgc gga gtc cac acg ggc ttc cgc aat gcc tgg            541
Ser Tyr Val Arg Asp Cys Gly Val His Thr Gly Phe Arg Asn Ala Trp
100             105                 110                 115 gat gag att gcc cag cgc gcg agg gac gcc gtt gcc aag gcc cgc gcc            589
Asp Glu Ile Ala Gln Arg Ala Arg Asp Ala Val Ala Lys Ala Arg Ala
                120                 125                 130 atg aac ccg tcc tac aag gtc atc tcc acg ggc cac tct ctc ggc ggt            637
Met Asn Pro Ser Tyr Lys Val Ile Ser Thr Gly His Ser Leu Gly Gly
            135                 140                 145 gct gtc gca act ctg ggt gcc gct gac ctg agg tcc aag gga acc gca            685
Ala Val Ala Thr Leu Gly Ala Ala Asp Leu Arg Ser Lys Gly Thr Ala
        150                 155                 160 gtt gac atc ttc acc ttt ggt gct ccc cgt gta ggc aac gct gaa ctc            733
Val Asp Ile Phe Thr Phe Gly Ala Pro Arg Val Gly Asn Ala Glu Leu
165                 170                 175 tca gca ttc atc acg gcc cag gcc ggc ggc gag ttc cgt gtc act cat            781
Ser Ala Phe Ile Thr Ala Gln Ala Gly Gly Glu Phe Arg Val Thr His
180             185                 190                 195 ggc cgt gat ccc gtg ccc cgt ctg cct ccc atc gtc ttt ggc tac aga            829
Gly Arg Asp Pro Val Pro Arg Leu Pro Pro Ile Val Phe Gly Tyr Arg
                200                 205                 210 cac aca tcg ccc gag tac tgg ctg gcc ggc ggt gca tcc acc aag atc            877
His Thr Ser Pro Glu Tyr Trp Leu Ala Gly Gly Ala Ser Thr Lys Ile
            215                 220                 225 gac tac tcc gtc aac gac atc aag gtc tgt gaa ggc gcc gcc aat ctc            925
Asp Tyr Ser Val Asn Asp Ile Lys Val Cys Glu Gly Ala Ala Asn Leu
        230                 235                 240 gcc tgc aac ggc ggt aca cta ggc ctg gat atc atc gct cat ctg cgc            973
Ala Cys Asn Gly Gly Thr Leu Gly Leu Asp Ile Ile Ala His Leu Arg
245                 250                 255 tac ttc cag aac acc gat gcc tgc aca gcg ggc ggt atc tcg tgg aag            1021
Tyr Phe Gln Asn Thr Asp Ala Cys Thr Ala Gly Gly Ile Ser Trp Lys
260             265                 270                 275 aga ggg gac aag gcc aag cgt gac gag atc ccc aag cgc cag gag ggc            1069
Arg Gly Asp Lys Ala Lys Arg Asp Glu Ile Pro Lys Arg Gln Glu Gly
                280                 285                 290 atg acg gat gag gag ttg gag cag aag ctc aac gac tat gtc gcc atg            1117
Met Thr Asp Glu Glu Leu Glu Gln Lys Leu Asn Asp Tyr Val Ala Met
            295                 300                 305 gac aag gag tac gtg gac agc cat aag atc tag                                1150
Asp Lys Glu Tyr Val Asp Ser His Lys Ile
        310                 315

<210> SEQ ID NO 2
<211> LENGTH: 348
<212> TYPE: PRT
<213> ORGANISM: Fusarium solani

<400> SEQUENCE: 2

Met Arg Leu Leu Pro Leu Leu Ser Val Val Thr Leu Thr Ala Ala Ser
```

```
            -30                 -25                 -20
Pro Ile Ala Ser Val Gln Glu Tyr Thr Asp Ala Leu Glu Lys Arg Ala
-15             -10                 -5              -1   1

Ile Thr Ala Ser Gln Leu Asp Tyr Glu Asn Phe Lys Phe Tyr Ile Gln
            5                   10                  15

His Gly Ala Ala Ala Tyr Cys Asn Ser Glu Thr Ala Ser Gly Gln Lys
            20                  25                  30

Ile Thr Cys Asn Asp Asn Gly Cys Lys Gly Ile Glu Ala Asn Asn Ala
        35                  40                  45

Ile Ile Val Ala Ser Phe Val Gly Thr Gly Thr Gly Ile Gly Gly Tyr
50                  55                  60                  65

Val Ser Thr Asp Asn Val Arg Lys Glu Ile Val Leu Ser Ile Arg Gly
                70                  75                  80

Ser Ser Asn Ile Arg Asn Trp Leu Thr Asn Val Asp Phe Gly Gln Ser
            85                  90                  95

Ser Cys Ser Tyr Val Arg Asp Cys Gly Val His Thr Gly Phe Arg Asn
            100                 105                 110

Ala Trp Asp Glu Ile Ala Gln Arg Ala Arg Asp Ala Val Ala Lys Ala
    115                 120                 125

Arg Ala Met Asn Pro Ser Tyr Lys Val Ile Ser Thr Gly His Ser Leu
130                 135                 140                 145

Gly Gly Ala Val Ala Thr Leu Gly Ala Ala Asp Leu Arg Ser Lys Gly
                150                 155                 160

Thr Ala Val Asp Ile Phe Thr Phe Gly Ala Pro Arg Val Gly Asn Ala
                165                 170                 175

Glu Leu Ser Ala Phe Ile Thr Ala Gln Ala Gly Gly Glu Phe Arg Val
            180                 185                 190

Thr His Gly Arg Asp Pro Val Pro Arg Leu Pro Pro Ile Val Phe Gly
    195                 200                 205

Tyr Arg His Thr Ser Pro Glu Tyr Trp Leu Ala Gly Gly Ala Ser Thr
210                 215                 220                 225

Lys Ile Asp Tyr Ser Val Asn Asp Ile Lys Val Cys Glu Gly Ala Ala
                230                 235                 240

Asn Leu Ala Cys Asn Gly Gly Thr Leu Gly Leu Asp Ile Ile Ala His
            245                 250                 255

Leu Arg Tyr Phe Gln Asn Thr Asp Ala Cys Thr Ala Gly Gly Ile Ser
        260                 265                 270

Trp Lys Arg Gly Asp Lys Ala Lys Arg Asp Glu Ile Pro Lys Arg Gln
275                 280                 285

Glu Gly Met Thr Asp Glu Leu Glu Gln Lys Leu Asn Asp Tyr Val
290                 295                 300                 305

Ala Met Asp Lys Glu Tyr Val Asp Ser His Lys Ile
                310                 315
```

<210> SEQ ID NO 3
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(21)
<223> OTHER INFORMATION: n = A,T,C,G

<400> SEQUENCE: 3
acaggccact cccttggagg ngc                                            23

<210> SEQ ID NO 4
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n in position 19 = A,T,C,G
<220> FEATURE:
<221> NAME/KEY: misc_feature
<222> LOCATION: (19)..(19)
<223> OTHER INFORMATION: n  = A,T,C,G

<400> SEQUENCE: 4
aggagggaga cgggggacng grtc                                           24

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
gctgaactct cagcattcat cacggccc                                       28

<210> SEQ ID NO 6
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 071200j2

<400> SEQUENCE: 6
ccaaaggtga agatgtcaac tgcggttc                                       28

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 221200j1

<400> SEQUENCE: 7
cggcggcgag ttccgtgtca ctcatg                                         26

<210> SEQ ID NO 8
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 221200j2

<400> SEQUENCE: 8
gacctcaggt cagcggcacc cagag                                          25

<210> SEQ ID NO 9
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 170101j11

<400> SEQUENCE: 9
cttgaagttt tcatagtcaa gttgagag                                         28

<210> SEQ ID NO 10
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 290101j2

<400> SEQUENCE: 10
actagcctcg agctagatct tatggctgtc cacgtactc                             39

<210> SEQ ID NO 11
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 020301j1

<400> SEQUENCE: 11
gcgcgcggat ccaccatgcg cctgcttcct ctcctctcgg tcgta                      45

<210> SEQ ID NO 12
<211> LENGTH: 21
<212> TYPE: DNA
<213> ORGANISM: Fusarium solani
<220> FEATURE:
<221> NAME/KEY: misc_feature
<223> OTHER INFORMATION: 19670

<400> SEQUENCE: 12
ccccatcctt taactatagc g                                                21

<210> SEQ ID NO 13
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: 19671

<400> SEQUENCE: 13
ctcccttctc tgaacaataa accc                                             24

LIPOLYTIC ENZYME

CROSS-REFERENCE TO RELATED APPLICATIONS

This application claims, under 35 U.S.C. 119, priority of Danish application no. PA 2001 00843 filed May 25, 2001, the contents of which are fully incorporated herein by reference.

FIELD OF THE INVENTION

The present invention relates to a nucleic acid sequence encoding a lipolytic enzyme from *Fusarium solani*, as well as a recombinant method of producing the lipolytic enzyme.

BACKGROUND OF THE INVENTION

Lipolytic enzymes (such as lipases and phospholipases) are known to be useful, e.g., in baking and detergents.

U.S. Pat. No. 5,990,069 discloses a lipase from a strain of *Fusarium solani* var. *minus*. A lipase/phospholipase from *Fusarium oxysporum* and its sequence are disclosed in WO 98/26057.

SUMMARY OF THE INVENTION

The inventors have isolated a gene encoding a lipolytic enzyme from *Fusarium solani* MUCL 38667 and cloned it into an *E. coli* strain. Accordingly, the invention provides a DNA sequence encoding a lipolytic enzyme.

The nucleic acid sequence of the invention may comprise a nucleic acid sequence which encodes a lipolytic enzyme and comprises:
  a) the DNA sequence encoding a mature lipolytic enzyme cloned into a plasmid present in *Escherichia coli* DSM 14361,
  b) the DNA sequence encoding a mature lipolytic enzyme shown in SEQ ID NO: 1, or
  c) an analogue of the DNA sequence defined in a) or b) which
    i) has at least 80% identity with said DNA sequence, or
    ii) hybridizes at high stringency with said DNA sequence, its complementary strand or a subsequence thereof.

Other aspects of the invention provide a recombinant expression vector comprising the DNA sequence, and a cell transformed with the DNA sequence or the recombinant expression vector. The invention also provides a recombinant methods of producing the lipolytic enzyme.

A comparison with full-length prior-art sequences shows that the mature amino acid sequence of the lipolytic enzyme from *Fusarium solani* has 66% identity with the lipase/phospholipase from *Fusarium oxysporum* described above, and the corresponding DNA sequences show 68% identity.

DETAILED DESCRIPTION OF THE INVENTION

Genomic DNA Source

The DNA sequence of the invention may be isolated from *Fusarium solani* MUCL 38667 or from *Escherichia coli* DSM 14361

MUCL 38667 is available on commercial terms from Mycothèque de l'Université Catholique de Louvain, Place Croix du Sud 3, B-1348 Louvain-la-Neuve, Belgium by referring to U.S. Pat. No. 5,990,069.

*E. coli* DSM 14361 contains a plasmid with a gene encoding the lipolytic enzyme. It was deposited by the inventors on DSM 14361 under the terms of the Budapest Treaty with the DSMZ—Deutshe Sammlung von Microorganismen und Zellkulturen GmbH, Mascheroder Weg 1b, D-38124 Braunschweig DE, Germany.

Lipolytic Enzyme

The lipolytic enzyme encoded by the DNA sequence of the invention is able to hydrolyze carboxylic ester bonds and is classified as EC 3.1.1 according to Enzyme Nomenclature 1992, Academic Press, Inc. The enzyme has lipase (triacylglycerol lipase) activity (EC 3.1.1.3) and may also have phospholipase activity.

Further properties of the lipolytic enzyme are described in U.S. Pat. No. 5,990,069.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipolytic enzyme of the invention may be produced by transforming a suitable host cell with a DNA sequence encoding the lipolytic enzyme, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, e.g. a strain of Aspergillus, Fusarium, Trichoderma or Saccharomyces, particularly *A. niger, A. oryzae, F. graminearum, F. sambucinum, F. cerealis* or *S. cerevisiae*. The production of the lipolytic enzyme in such host organisms may be done by the general methods described in EP 238,023 (Novo Nordisk), WO 96/00787 (Novo Nordisk) or EP 244,234 (Alko).

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at approx. 45° C. The filter is then washed two times for 30 minutes in 2×SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using an x-ray film.

Alignment and Identity

The lipolytic enzyme and the nucleotide sequence of the invention may have identity to the disclosed sequences of at least 85%, particularly at least 90% or at least 95%, e.g. at least 98%.

For purposes of the present invention, alignments of sequences and calculation of identity scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98).

Lipase Activity (LU)

A substrate for lipase is prepared an emulsion of 5% by volume of tributyrin (glycerin tributyrate) using 0.1% gum Arabic as emulsifier. The hydrolysis of tributyrin at 30° C. at pH 7 is followed in a pH-stat titration experiment. One unit of lipase activity (1 LU) equals the amount of enzyme capable of releasing 1 µmol butyric acid/min at the standard conditions. 1 KLU=1000 LU.

Use of Lipolytic Enzyme

The lipolytic enzyme of the invention can be used in various industrial application of lipolytic enzymes, e.g. in baking, detergents, diglyceride synthesis (EP 307154), acidolysis, interesterification (WO 8802775), ester hydrolysis, oil degumming (JP-A 2-153997, U.S. Pat. No. 5,264,367), production of lysolecithin (JP patent 2794574, JP-B 6-087751) and in the process described in PCT/DK 00/00109.

Use in Baking

The lipolytic enzyme of the invention can be used in the preparation of dough, bread and cakes, e.g. to improve the elasticity of the bread or cake. Thus, the lipolytic enzyme can be used in a process for making bread, comprising adding the lipolytic enzyme to the ingredients of a dough, kneading the dough and baking the dough to make the bread. This can be done in analogy with WO 9404035 and EP 585988.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

EXAMPLES

Example 1

Cloning of a Phospholipase Gene from the *Fusarium solani* Strain MUCL 38667

A genomic DNA preparation of the strain MUCL 38667 was made as described in WO 00/24883.

A PCR reaction (96° C. 5 min, 30* (94° C. 30 sec., 55° C. 30 sec, 72° C. 1 min), 72° C. 5 min) was run using PWO polymerase in 2.5 mM $MgSO_4$ as recommended by the manufacturer (Boehringer Mannheim) with the MUCL 38667 genomic DNA as template, with oligo 161000J1 and 161000J2 (SEQ ID NO: 3 and 4). These oligo'es were designed based conserved sequences in homologous phospholipases.

A fragment of 180 bp was isolated from a 2% gel. Because the amounts of DNA was very small, a new identical pcr was run, this time using the 180 bp fragment as template rather than MUCL 38667 genomic DNA.

This fragment was cloned into pCR4 using TOPO-cloning as recommended by the manufacture (Invitrogen) and transformed into the *E. coli* strain TOPO10.

DNA preparations where made using the Qiagen minispinprep kit and the clones where sequenced using M13 rev and M13 fwp primer supplied with the TOPO-cloning kit (Invitrogen). Sequence alignment was made to all available DNA sequence using SRS. The 180 bp fragment was identified as originating from a phospholipase gene.

Based on the 180 bp fragment DNA sequence, four primers were designed: 071200J1, 071200j2, 221200J1, 221200J2 (SEQ ID NO: 5-8).

The MUCL38667 genomic DNA (app. 1 µg) was cut with AgeI in a volume of 10 µl and ligated in a volume of 500 µl. The DNA was precipitated in ethanol and redisolved in water. 2 µl of the religated mix was used as template, and oligo 071200J1 and 071200J2 in a PCR reaction using GeneAMP XL PCR kit as recommended by manufacture (Boehringer Mannheim) in a total of 20 µl.

1 µl of this PCR reaction fragments was used as template in a second PCR reaction using nested oligoes 221200J1 and 221200J2 (SEQ ID NO: 5 and 6), which was identical to the above mentioned.

The generated PCR fragment of app. 1500 bp was cloned into pCR4 using TOPO-cloning as recommended by the manufacture (Invitrogen) and transformed into the *E. coli* strain TOPO10.

DNA preparations where made using the Qiagen minispinprep kit and the clones where sequenced using M13 rev and M13 fwp primer supplied with the TOPO-cloning kit (Invitrogen). Sequence alignment was made to all available DNA sequence using SRS. The 1500 bp fragment was identified as originating from the 3' end of a phospholipase gene.

Based on the 1500 bp fragment DNA sequence, one primer was designed: 170101J11 (SEQ ID NO: 9).

The MUCL 38667 genomic DNA (app. 1 μg) was cut with HindIII in a volume of 10 μl and ligated in a volume of 500 μl. The DNA was precipitated in ethanol and redissolved in water. 2 μl of the religated mix was used as template, and oligo 221200J1 and 170101J11 in a PCR reaction using GeneAMP XL PCR kit as recommended by manufacture (Boehringer Mannheim) in a total of 20 μl.

The generated PCR fragment of app. 350 bp was cloned into pCR4 using TOPO-cloning as recommended by the manufacture (Invitrogen) and transformed into the E. coli strain TOPO10.

DNA preparations were made using the Qiagen minispin-prep kit and the clones where sequenced using T3 and T7 primer supplied with the TOPO-cloning kit (Invitrogen). Sequence alignment was made to all available DNA sequence using SRS. The 350 bp fragment was identified as originating from the 5' end of a phospholipase gene.

Based on the 350 bp and the 1500 bp DNA sequence, two primers were designed (290101j2 and 020301j1, SEQ ID NO: 10 and 11), thus covering the hole gene.

A PCR reaction (96° C. 5 min, 30* (94° C. 30 sec., 55° C. 30 sec, 72° C. 2 min), 72° C. 5 min) was run using PWO polymerase in 2.5 mM $MgSO_4$ as recommended by manufacture (Boehringer Mannheim) with the MUCL38667 genomic DNA as template, with oligo 290101J2 and 020301J1 (SEQ ID NO: 10 and 11).

The generated PCR fragment of app. 1100 bp were cloned into pCR4 using TOPO-cloning as recommended by the manufacture (Invitrogen) and transformed into the E. coli strain TOPO10.

DNA preparations were made using the Qiagen minispin-prep kit and the clones where sequenced using T3 and T7 primer supplied with the TOPO-cloning kit (Invitrogen). Sequence alignment was made to all available DNA sequence using SRS, as well as earlier sequence of the same.

Example 2

Construction of Expression Vector and Transformation into Aspergillus oryzae

The cloned phospholipase gene in the TOPO vector, as well as pJVi9 (WO 97/47746) was cut with the restriction enzymes BamHI and XhoI. The pJVI9 vector and the phospholipase gene were purified from a 1% agarose gel, and ligated o/n.

The ligation was transformed into the E.coli strain DH10b, and transformants were isolated.

DNA preparations where made using the Qiagen minispinprep kit and the clones where verified by sequencing using 19670 and 19671 primer (SEQ ID NOS: 12 and 13).

The resulting plasmid was transformed into the Aspergillus oryzae strain Jal125 (WO 97/35956) using the following method:

Transformation of Aspergillus oryzae (General Procedure)

100 ml of YPD (Sherman et al., (1981), Methods in Yeast Genetics, Cold Spring Harbor Laboratory) are inoculated with spores of A. oryzae and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH 5.8. The suspension is cooled on ice and 1 ml of buffer containing 120 mg of Novozym® 234 is added. After 5 min., 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the $MgSO_4$ cushion. 2 volumes of STC (1.2 M sorbitol, 10 mM Tris-HCl, pH 7.5, 10 mM $CaCl_2$) are added to the protoplast suspension and the mixture is centrifuged for 5 min. at 1000 g. The protoplast pellet is resuspended in 3 ml of STC and repelleted. This is repeated. Finally, the protoplasts are resuspended in 0.2–1 ml of STC.

100 μl of protoplast suspension are mixed with 5–25 μg of p3SR2 (an A. nidulans amdS gene carrying plasmid described in Hynes et al., Mol. and Cel. Biol., Vol. 3, No. 8, 1430–1439, August 1983) and 5 μg of the pJVI9-phospholipase plasmid in 10 μl of STC. The mixture is left at room temperature for 25 min. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2M sorbitol. After one more sedimentation the protoplasts are spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37° C. spores are picked, suspended in sterile water and spread for single colonies.

12 independent transformants from the pJVI9-phorpholipase transformations were isolated on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth, and at the same time inoculated into a 96-well microtiter dish containing 200 μl minimal media of 1*vogel, 2% maltose (e.g., Methods in Enzymology, Vol. 17 p. 84) in each well.

After three days of incubation at 34° C., media from the cultures in the microtiter dish were assayed for lipase activity. A 10 μl aliquot of media from each well was added to a microtiter well containing 200 μl of a lipase substrate of 0.018% p-nitrophenylbutyrate, 0.1% Triton X-100, 10 mM $CaCl_2$, 50 mM Tris pH 7.5. Activity was assayed spectrophotometrically at 15-second intervals over a five minute period, using a kinetic microplate reader (Molecular Device Corp., Sunnyvale Calif.), using a standard enzymology protocol (e.g., *Enzyme Kinetics,* Paul C. Engel, ed., 1981, Chapman and Hall Ltd.) Briefly, product formation is measured during the initial rate of substrate turnover and is defined as the slope of the curve calculated from the absorbance at 405 nm every 15 seconds for 5 minutes.

This procedure was repeated and spores of the best producing transformants after the second re-isolation were stored as a defined transformant.

*A. oryzae* JaL 125 (WO 97/35956) is derived from *Aspergillus oryzae* IFO 4177 available from Institute for Fermention, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p. 2807–2811) deleted by a one step gene replacement method (described by G. May in "Applied Molecular Genetics of Filamentous Fungi" (1992), p. 1–25. Eds. J. R. Kinghorn and G. Turner; Blackie Academic and Professional), using the *A. oryzae* pyrG gene as marker.

What is claimed is:

1. A nucleic acid sequence which comprises:
   a) the DNA sequence encoding a mature lipolytic enzyme cloned into a plasmid present in *Eseherichia coli* DSM 14361,
   b) the DNA sequence encoding a mature lipolytic enzyme shown in SEQ ID NO: 2,
   c) an analogue of the sequence defined in a) or b) which encodes a lipolytic enzyme and
      i) has at least 95% identity with said DNA sequence, or
      ii) hybridizes with a complementary strand of said a) or SEQ ID NO:1 under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 70° C., or
   d) a complementary strand of a), b) or c).

2. A nucleic acid construct comprising the nucleic acid sequence of claim 1 operably linked to one or more control sequences capable of directing the expression of the lipolytic enzyme in a suitable expression host.

3. A recombinant expression vector comprising the nucleic acid construct of claim 2, a promoter, and transcriptional and translational stop signals.

4. A recombinant host cell comprising the nucleic acid construct of claim 2.

5. A method for producing a lipolytic enzyme comprising cultivating the host cell of claim 4 under conditions conducive to produce the lipolytic enzyme, and recovering the lipolytic enzyme.

6. The DNA sequence of claim 1, which comprises the DNA sequence encoding a mature lipolytic enzyme cloned into a plasmid present in *Escherichia coli* DSM 14381.

7. The DNA sequence of claim 1, which encodes the mature lipolytic enzyme shown in SEQ ID NO: 2.

8. The DNA sequence of claim 1, which has at least 95% identity with the DNA sequence of said (a) or said SEQ ID NO:1.

9. The DNA sequence of claim 1, which hybridizes with a complementary strand of said a) or SEQ ID NO:1 under hybridization conditions comprising prehybridizing in a solution of 6×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 70° C.

* * * * *